United States Patent [19]
Barrows

[11] Patent Number: 6,120,788
[45] Date of Patent: Sep. 19, 2000

[54] BIOABSORBABLE TRIGLYCOLIC ACID POLY(ESTER-AMIDE)S

[75] Inventor: Thomas Harry Barrows, Pepperell, Mass.

[73] Assignee: BioAmide, Inc., St. Paul, Minn.

[21] Appl. No.: 09/174,136

[22] Filed: Oct. 16, 1998

Related U.S. Application Data

[60] Provisional application No. 60/062,064, Oct. 16, 1997.

[51] Int. Cl.$^7$ .............................. A61L 17/00; C08G 69/44
[52] U.S. Cl. ........................... 424/426; 528/291
[58] Field of Search .............................. 528/291; 424/426

[56] References Cited

U.S. PATENT DOCUMENTS

| | | | |
|---|---|---|---|
| 2,946,769 | 7/1960 | Rose | 528/291 |
| 3,025,323 | 3/1962 | Rose et al. . | |
| 4,209,607 | 6/1980 | Shalaby | 528/291 |
| 4,226,243 | 10/1980 | Shalaby et al. . | |
| 4,343,931 | 8/1982 | Barrows | 528/291 |
| 4,429,080 | 1/1984 | Casey et al. . | |
| 4,529,792 | 7/1985 | Barrows . | |
| 5,522,841 | 6/1996 | Roby et al. | 606/230 |

OTHER PUBLICATIONS

Katayama, et al. "Synthesis of Alternating Polyamide Esters by Melt and Solution Polycondensations of N,N'–Di(6–hydroxycaproyl) dimines and N–6–Hydroxycaproyl Aminoalcohol with Terephthalic and Adipic Dimethyl Esters and Dichlorides" *J. of Applied Polymer Science*; 20: 975–994.

*Primary Examiner*—Peter F. Kulkosky
*Attorney, Agent, or Firm*—Michael Best & Friedrich LLP; Grady J. Frenchick; Karen B. King

[57] ABSTRACT

This invention relates to fiber-forming bioabsorbable poly (ester-amide)s made by the polymerization of diamidediols with 3,6-dioxaoctanedioic acid, also known as "triglycolic acid". More specifically it relates to diol terminated poly (ester-amide)s of triglycolic acid that are optionally further reacted with glycolide, lactide, trimethylene carbonate, epsilon-caprolactone, or p-dioxanone, or mixtures of said cyclic monomers to produce the corresponding block copolymers. Said polymers are useful in the production of surgical sutures having superior performance characteristics including low bending stiffness and in the production of other fiber-based bioabsorbable implants and molded devices.

13 Claims, No Drawings

BIOABSORBABLE TRIGLYCOLIC ACID POLY(ESTER-AMIDE)S

CROSS-REFERENCE TO RELATED APPLICATIONS

This application claims the benefit of U.S. Provisional Application Ser. No. 60/062,064, filed Oct. 16, 1997.

STATEMENT REGARDING FEDERALLY SPONSORED RESEARCH OR DEVELOPMENT

Not applicable.

FIELD OF THE INVENTION

This invention relates to new and useful fiber-forming biabsorbable polymeric materials, such as bioabsorbable triglycolic acid poly(ester-amides)s, derived from reacting diamidediols with a diacid chloride deriviative of 3,6-dioxaoctanedioic acid, also known as "triglycolic acid". This invention also relates to new and useful diol terminated poly(ester-amide)s of triglycolic acid made by the polymerization of diamine diols with triglycolic acid poly(ester-amides)s, and to products of reacting such diol terminated poly(ester-amide)s with cyclic monomers to produce block copolymers. This invention further relates to methods of making new and useful fiberous bioabsorbable implants, including surgical sutures and molded devices, of such block copolymers or other polymeric materials.

BACKGROUND OF THE INVENTION

Since the first synthetic absorbable suture made from braided multifilaments of poly(glycolic acid) was introduced in about the year 1970, advancements in the design and synthesis of bioabsorbable polymers have resulted in continuous improvements in absorbable suture products.

In addition to the suture application, high strength, highly flexible, tough, and durable fibers that possess a prolonged flex fatigue life are needed for use as braided, knitted, woven, or non-woven implants to augment and temporarily reinforce autologous tissue grafts or to serve as scaffolds for tissue regeneration. One example of such an implant is known as a ligament augmentation device (LAD) used to reconstruct the anterior cruciate ligament (ACL) of the knee. Bioabsorbable fibers of the prior art, such as poly(L-lactic acid) (PLA), have not been successful in this application due to low flex fatigue life, shedding of wear debris due to the brittle nature of the fibers, and prolonged bioabsorption time.

Other well known uses for bioabsorbable polymers that have not been fully realized or perfected with available polymers of the prior art include scaffolds for tissue engineering, bioabsorbable knitted vascular grafts, drug-releasing devices, growth factor-releasing implants for bone and tissue regeneration, and fiber-reinforced composites for orthopedic applications. For example, composites of polymers reinforced with dissimilar materials, such as dissolvable glass fiber reinforced poly(lactic acid) are unacceptable for use as implants, the following reasons. Although dissolvable glass fibers provide high modulus needed for the composite to have high initial strength and stiffness, adhesion between glass and polymer invariably fails prematurely in vivo resulting in devices with unacceptable in vivo performance.

Self-reinforced composites were developed as an alternative to composites of polymers reinforced with dissimilar materials, such as those described above. In self-reinforced fiber composites both reinforcing fibers and matrix are made of the same material. Although the stiffness is lower than can be achieved with glass fibers, this alternative type of composite ensures good adhesion between fiber and matrix and thus offers the possibility of longer lasting in vivo strength. Self-reinforced poly(glycolic acid) (PGA) rods, pins and screws made by hot pressing or sintering PGA fibers have shown promise in clinical use. The main disadvantage of PGA in general is that it degrades too fast for orthopedic applications and releases an excessive concentration of acidic degradation products into the surrounding tissue.

Despite the advancements in the art of producing polymeric materials and methods for making polymeric materials suitable for use in sutures, molded devices, and similar surgical devices. Specifically, there continues to be a need for new fibers that are monofilament, have high initial tensile knot strength, retain useful strength in vivo for about two weeks or longer, are fully bioabsorbed within a few months after strength loss, and have very low bending stiffness.

BRIEF SUMMARY OF THE INVENTION

The present invention consists of a biabsorbable polymer of the general formula (I):

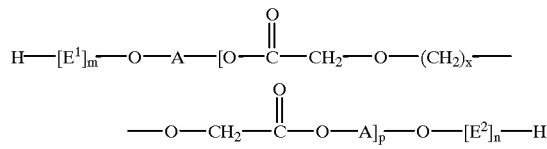

wherein, x is from 2 to 10, m and n are independently from 0 to 2000, p is from 10 to 2000, and A is comprised of from 0 to 90 mole % A1 in combination with other structures selected from the group consisting of A2 and A3, wherein:

A1 is defined by the formula (II): $-(CH_2)_y-$, wherein y is from 2 to 10;

A2 is defined by the formula (III):

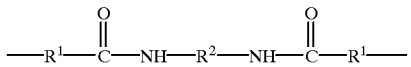

wherein $R^1$ is selected from the group consisting of:
i) a linear alkene having from 1 to 5 carbon atoms;
ii) an ester defined by the formula(IV): $-(CH_2)_{x1}-O-(CH_2)_{y1}-$, wherein x1 (the end attached to the amide carbonyl) is from 1 to 4 and y1 (the end attached to the ester oxygen) is independently from 2 to 6; and
iii) a benzyl alkane of the formula(V): $-(CH2)_{x2}-C_6H_4-$ wherein the $-(CH_2)_{x2}$ end of the benzyl alkane is covalently attached to the amide carbonyl of formula III, and x2 is from 0 to 1; and
iv) an alkyl benzyl ester of the formula(VI): $-(CH_2)_{x3}-C_6H_4-O-(CH_2)_{y3}-$, wherein the $-(CH_2)_{x3}$ end of the alkyl benzyl ester is attached to the amide carbonyl of formula III, x3 is from 0 to 1, the $(CH_2)_{y3}-$ end of the alkyl benzyl ester is attached to the ester oxygen of formula I, and y3 is independently from 2 to 6; and $R^2$ is selected from the group consisting of linear alkylenes having from 2 to 10 carbon atoms; and A3 is defined by the following structure:

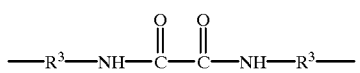

wherein $R^3$ is a divalent aliphatic or aromatic hydrocarbon radical having from 3 to about 8 carbon atoms; and $E^2$ is defined by a formula selected from the group of formulae consisting of:
formula (V): [—CO—CHR$^4$—O—], wherein $R^4$ is selected from the group consisting of —H (from glycolide) and —CH$_3$ (from lactide);
formula (VI): [—CO—O—(CH$_2$)$_3$—O—];
formula (VII): [—CO—CH$_2$—O—(CH$_2$)$_2$—O—];
formula (VIII): [—CO—(CH$_2$)$_5$—O—]; and
combinations of formula V to VIII; and $E^1$ has the same structure as $E^2$ except that the orientation of the formula of $E^1$ is reversed.

In an alternative embodiment, the invention is the bioabsorbable polymer of general formula (I), above, wherein x is 2, and except as indicated all the other variables in the formula are defined as described above, except that:

A2 is defined by formula (III):

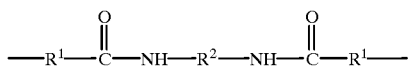

wherein: $R^1$ is selected from the group consisting of:
i) a linear alkene having from 1 to 5 carbon atoms;
ii) an ester defined by formula(IV): —(CH$_2$)$_{x1}$—O—(CH$_2$)$_{y1}$—, wherein the —(CH$_2$)$_{x1}$, end of the ester is attached to the amide carbonyl of formula (III), x1 is from 1 to 4 and y1 is independently from 2 to 6;
iii) a benzyl alkane of formula(V):

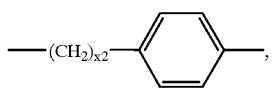

wherein the —(CH$_2$)$_{x2}$ end of the benzyl alkane is covalently attached to the amide carbonyl of formula III, and x2 is from 0 to 1; and
iv) an alkyl benzyl ether of formula(VI):

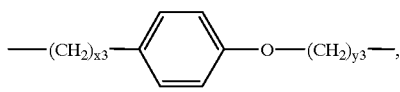

wherein the —(CH$_2$)$_{x3}$ end of the alkyl benzyl ester is attached to the amide carbonyl of formula III, x3 is from 0 to 1, the (CH$_2$)$_{y3}$— end of the alkyl benzyl ester is attached to the ester oxygen of formula I, and y3 is independently from 2 to 6; and $R^2$ is selected from the group consisting of linear alkyenes having from 4 to 10 carbon atoms.

The present invention also consists of bioabsorbable materials made from the bioabsorbable polymer of the invention designed for in vivo use or implantation, including but not limited to bioabsorbable sutures, and a self-reinforced device comprised of fused or sintered fibers of the bioabsorbable polymer. The present invention further consists of a method of making self-reinforced materials from the bioabsorbable polymer of this invention.

DETAILED DESCRIPTION OF THE INVENTION

The diacid chloride derivative of 3,6-dioxaoctanedioic acid, commonly known as "triglycolyl chloride", has been discovered in the present invention to be an ideal monomer or comonomer for polymerization with diamidediols to produce poly(ester-amide)s capable of forming flexible, tenacious monofilament fibers with adequate bioabsorption time for use as surgical suture. Triglycolic acid is inexpensive and readily available since it can be economically produced by nitric acid oxidation of triethylene glycol. The conversion of triglycolic acid into triglycolyl chloride is described in U.S. Pat. No. 3,966,766, the teachings of which are incorporated herein (see Example 1, "Preparation of triglycolyl chloride").

Since polymers formed by polymerization of diamidediols with triglycolyl chloride are expected to have low softening points, it may not be feasible to use the suspension polymerization method described in U.S. Pat. No. 5,286,837, the teachings of which are incorporated herein. This method fails to yield high molecular weight product if the diamidediol suspension "melts down" due to low oligomer melting point. In this case an alternative method of forming poly(ester-amide)s from diacid chlorides and diamidediols in solution can be utilized (see S. Katayama et al., *Journal of Applied Polymer Science*, 20, 975–994 (1976), incorporated herein by reference).

An alternative method of forming triglycolic acid poly(ester-amide)s that may be preferable to the use of triglycolyl chloride is to melt polyesterify the diamidediol by reacting it with the dimethyl ester or diethyl ester of triglycolic acid with an appropriate catalyst and with distillation of methanol or ethanol, respectively, as the condensation reaction byproduct. If a slight excess of diamidediol is used, the final reaction conditions of high temperature and low pressure will remove traces of alcohol and any unreacted dimethyl or diethyl triglycolate to give a diol terminated poly(ester-amide). Another method for producing diol terminated poly(ester-amide)s with improved molecular weight is described in U.S. Pat. Nos. 4,209,607 and 4,226,243, the teachings of which are incorporated herein. In this procedure an excess of an aliphatic diol having greater volatility than the diamidediol is added with an appropriate catalyst to an equamolar mixture of diamidediol and diacid diester. As the mixture is heated under conditions of increasing temperature and decreasing pressure, excess aliphatic diol is distilled from the mixture along with the condensation reaction byproduct alcohol to give exceptionally high molecular weight poly(ester-amide) that is diol terminated.

Since it is known that molten glycolide and molten lactide are solvents for poly(ester-amide)s (see U.S. Pat. No. 5,502,092, the teachings of which are incorporated herein), glycolide, lactide, or other cyclic monomers or mixtures of cyclic monomers and the appropriate catalyst (e.g. stannous octoate) can be added to the molten polymer to initiate the polymerization of polyglycolide or polylactide or other polymeric end blocks on the diol terminated poly(ester-amide). This process serves both to increase the polymer molecular weight and to introduce highly crystalline "hard segments" (in the case of glycolide or L-lactide) into the low $T_g$, soft, rubbery, yet strong and tough, ether containing poly(ester-amide). This type of polymer can be readily freed of unreacted glycolide or lactide, purified, and extruded into monofilament suture by well known methods. Procedures applicable to the synthesis of polyglycolide block copolymers of the present invention are described in U.S. Pat. Nos. 4,429,080; 5,133,739; 5,403,347; and 5,522,841, the teachings of which are incorporated herein.

1,6-Di(hydroxyacetamido)hexane, is a preferred diamidediol because it has been reported to have passed various safety and toxicity tests, is water soluble, yet does not contribute to premature fiber strength loss known to occur with shorter chain diamidediols such as 1,2-di (hydroxyacetamido)ethane.

Bioabsorption of poly(ester-amide)s of the present invention occurs at a reliable rate and is not limited by the choice of the diamidediol since the glycolate ester-like nature of the triglycolate moiety has been discovered in the present invention to be the primary structural feature controlling the rate of polymer hydrolysis. Thus diamidediols formed from ether containing hydroxy acids such as hydroxyethoxy acetic acid, hydroxytetramethyleneoxyacetic acid, and hydroxyhexamethyleneoxyacetic acid can be used to obtain diamidediols that have adequate water solubility and contain ether linkages for improved polymer flexibility. Alternatively, diamidediols also can be formed from hydroxyacids longer than glycolic acid that do not contain ether linkages. An example is 1,6-di(6-hydroxycaproamido)hexane formed by the reaction of 2 moles of caprolactone with 1 mole of hexamethylenediamine (see U.S. Pat. No. 3,025,323, the teachings of which are incorporated herein).

The preparation of hydroxyethoxyacetic acid as a precursor for p-dioxanone used in the synthesis of poly(dioxanone) has been described in U.S. Pat. No. 4,052,988, the teachings of which are incorporated herein. In this procedure sodium metal is reacted with an excess of ethylene glycol and then chloroacetic acid is added in an amount calculated to be one half the molar quantity of the sodium used. This gives the sodium salt of hydroxyethoxyacetic acid which can be converted into the free acid by precipitation of sodium chloride with HCl. At this point a diamine can be added to produce a "nylon salt" precursor of the desired diamidediol which can then be isolated and converted into the diamidediol by heating with distillation of water as described in U.S. Pat. No. 4,529,792, the teachings of which are incorporated herein. In a similar fashion other hydroxyalkyleneoxyacetic acid diamidediols can be obtained with the use of longer chain glycols such as tetramethylene glycol and hexamethylene glycol. In addition, chloroacids with longer methylene chain lengths also can be used in the reaction with glycols to give ether-containing hydroxy acids. For example, 3-chloropropionic acid, 4-chlorobutyric acid, and 5-chlorovaleric acid all can be used in place of chloroacetic acid to produce ether-containing hydroxy acids that are useful in the present invention.

Alternatively, if a stiff bioabsorbable polymer is desired for non-suture applications such as orthopedic fixation pins and rods, a rigid amidediol can be created for example by the reaction of one mole of a diamine with 2 moles of an aromatic hydroxyacid such as 4-hydroxybenzoic acid, 4-hydroxyphenylacetic acid, 4-hydroxyethoxybenzoic acid, 4-(hydroxyethoxy)phenylacetic acid, and the like. A distinct advantage of the present invention is that the chemical structure of the diamidediol is not limited to those structures that contribute to hydrolytic degradability of the polymer since hydrolytic degradablility is assured by the presence of triglycolic acid ester linkages. Methods of processing polymers of the present invention into useful forms include melt spinning of fibers, injection molding of parts, and hot pressing or sintering together bundles of fibers or plies of braided, woven, or non-woven fiber layers into self-reinforced composites. Fibers can also be processed into useful structural supports for example as bone fragment fixation devices and inter vertebral discs for spinal fusion by solvent welding. Thus a solution of the polymer can be made in a solvent that does not attack the crystalline regions of the fiber at room temperature. This solution can then be used to glue the fibers together. After evaporation of the solvent by vacuum drying, the composite can be further consolidated and strengthened by hot pressing at a temperature below the crystalline melting temperature of the fiber. This approach also allows for the uniform introduction of drugs or growth factors into the composite by suspending or dissolving the drug or growth factor into the polymer solution used for solvent welding.

An example of a bioabsorbable device made by this technique is a porous, fiber self-reinforced, bone growth factor-releasing implant for accelerated spinal fusion. Such devices are needed to eliminate the pain, morbidity, and expense associated with the use of autologous bone grafts to achieve spinal fusion.

Other methods of processing and utilizing polymers of the present invention will be apparent to those skilled in the art of polymer processing and surgical device fabrication.

DETAILED DESCRIPTION OF ILLUSTRATIVE EMBODIMENTS

The polymers of the present invention have a plurality of units of the general formula:

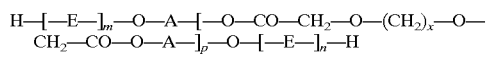

wherein x is from 2 to 10, m and n are independently from 0 to 2000, p is from 10 to 2000, and A is comprised of from 0 to 90 mole % B in combination with other structures selected from the group consisting of C and D wherein:

B is defined by the following structure:

wherein x is from 2 to 10; and
C is defined by the following structure:

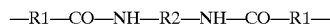

wherein:
a) R1 is selected from the group consisting of:
 i) linear alkylenes having from 1 to 5 carbon atoms; and
 ii) —(CH$_2$)$_x$—O—(CH$_2$)$_y$— wherein x (the end attached to the amide carbonyl) is from 1 to 4 and y (the end attached to the ester oxygen) is independently from 2 to 6; and
 iii) —(CH$_2$)$_x$—C$_6$H$_4$— wherein x (the end attached to the amide carbonyl) is from 0 to 1; and
 iv) —(CH$_2$)$_x$—C$_6$H$_4$—O—(CH$_2$)$_y$— wherein x (the end attached to the amide carbonyl) is from 0 to 1 and y (the end attached to the ester oxygen) is independently from 2 to 6; and
b) R2 is selected from the group consisting of linear alkylenes having from 2 to 10 carbon atoms; and
D is defined by the following structure:

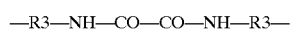

wherein R3 is a divalent aliphatic or aromatic hydrocarbon radical having from 3 to about 8 carbon atoms; and E is defined by the following structures:

I. [—CO—CHR4—O—] wherein R4 is selected from the group consisting of —H (from glycolide) and —CH$_3$ (from lactide);

II. [—CO—O—(CH$_2$)$_3$—O—]

III. [—CO—CH$_2$—O—(CH$_2$)$_2$—O—]

IV. [—CO—(CH$_2$)$_5$—O—]

and combinations thereof. Note that the above structures I. through IV. are drawn to represent replacement of E on the right side of the general formula and will be reversed for replacement of E on the left side of the general formula.

The preferred embodiments of the present invention are polymers with end blocks (E) of polyglycolide or polylactide wherein R1 is formed from glycolic acid or hydroxycaproic acid (e.g. via caprolactone), and R2 is —(CH$_2$)$_6$—. These polymers have the advantages of excellent initial fiber strength retention in vivo due to resistance of moisture uptake, complete bioabsorption due to amidediol water solubility and the proven bioabsorbability of commercially available glycolic and lactic acid ester containing polymers.

EXAMPLES

The following Examples are illustrative of the invention described above. Actual synthetic preparation of these and other example polymers may be performed according to the general instructions set forth below.

Example 1

Poly[2,5-dioxahexane-1,6-di(carbonyloxy)hexane-1, 6-di(amidocarbonylmethylene)]

Triglycolyl chloride is prepared according the procedure in U.S. Pat. No. 3,966,766, Example 1. 1,6-Di (hydroxyacetamido)hexane is prepared according to the method described in Example 1 of U.S. Pat. No. 4,343,931, the teachings of which are incorporated herein. These two monomers are then polymerized according to the solution polymerization method described in the literature (see S. Katayama, T. Murakami, Y. Takahashi, H. Serita, Y. Obuchi, and T. Ito, "Synthesis of alternating polyamide esters by melt and solution polycondensations of N,N'-di(6-hydroxycaproyl)diamines and N-6-hydroxycaproyl aminoalcohol with terephthalic and adipic methyl esters and dichlorides", *Journal of Applied Polymer Science*, 20, 975–994 (1976)).

Example 2

1,6-Hexanediol terminated poly[2,5-dioxahexane-1, 6-di(carbonyloxy)hexane-1,6-di (amidocarbonylmethylene)]

Triglycolic acid diethyl ester is prepared from purified 3,6-dioxaoctanedioic acid (e.g. recrystallized from ethyl acetate) by reaction with excess ethanol. An example of an acceptable method of forming the diethyl ester is refluxing the triglycolic acid in ethanol with sulfuric acid as a catalyst with the use of 3A molecular sieves for removal of water in a Soxhlet extractor (see Fieser & Fieser, "Reagents for Organic Synthesis", page 705, John Wiley and Sons, Inc., 1967). Vacuum distillation of the diethyl ester will yield a pure, colorless liquid suitable for polymerization. High purity (e.g. triple recrystallized) 1,6-di(hydroxyacetamido) hexane and an equamolar amount of redistilled diethyl triglycolate are reacted together with a 20% molar excess of 1,6-hexanediol and a catalytic amount of a titanate catalyst such as Tyzor TOT™ (E.I. du Pont de Nemours & Co., Wilminton, Del. 19898) as described in the procedure of U.S. Pat. No. 4,226,243 Example 6 (B & C), optimum conditions of time, temperature, and pressure to be determined. Distillation of excess 1,6-hexanediol yields a high molecular weight diol-terminate poly(ester-amide) suitable for extrusion into high strength, flexible, and fully bioabsorbable surgical suture.

Example 3

Block copolymer of polyglycolide with poly[2,5-dioxahexane-1,6-di(carbonyloxy)hexane-1,6-di (amidocarbonylmethylene)]

Example 2 is repeated except that after an acceptable molecular weight is obtained (e.g. inherent viscosity of about 0.6 to 0.9 in 2,2,2-trifluoroethanol at 0.5% concentration at 30° C.) and the last traces of alcohol, diol, and any unreacted diethyl triglycolate have been removed under high vacuum, the melted polymer is cooled to about 130° C. and about one part by weight of glycolide for each about 4 parts by weight of the poly(ester-amide) is added to the reactor along with an appropriate amount of catalyst such as stannous octoate. The reaction is then heated up to about 195 ° C. and additional glycolide is added and block copolymerized with the poly(ester-amide) according to the general procedure for this type of reaction described in U.S. Pat. No. 5,522,841 Examples 1, 2, and 3. The resultant block copolymer can then be further processed as necessary to remove any unreacted glycolide and or homopolymer and melt extruded into monofilament suture. Such suture has the advantage of exceptionally high strength and flexibility.

Example 4

Poly[2,5-dioxahexane-1,6-di(carbonyloxy))hexane-1,6-di(amidocarbonylmethyleneoxyethylene)]

The preparation of hydroxyethoxyacetic acid has been described in U.S. Pat. No. 4,052,988, the teachings of which are incorporated herein. In this procedure sodium metal is reacted with an excess of ethylene glycol and then chloroacetic acid is added in an amount calculated to be one half the molar quantity of the sodium used. This gives the sodium salt of hydroxyethoxyacetic acid which can be converted into the free acid by precipitation of sodium chloride with HCl. At this point hexamethylenediamine is added to produce a "nylon salt" precursor of the desired diamidediol which is then isolated and converted into the desired diamidediol by heating with distillation of water as described in U.S. Pat. No. 4,529,792, the teachings of which are incorporated herein. 1,6-Di(hydroxyethoxyacetamido)hexane alternatively can be prepared by heating 2 moles of p-dioxanone with one mole of hexamethylenediamine. The product is purified by recrystallization and vacuum dried. This diamidediol monomer is then polymerized with triglycolyl chloride as in Example 1.

Example 5

Poly[2,5-dioxahexane-1,6-di(carbonyloxy)butane-1, 4-di(amidocarbonyl-1,4-phenylene)]

1,4-Di(4-hydroxybenzamido)butane is prepared by heating 2 moles of 4-hydroxybenzoic acid with one mole of butanediamine with distillation of water. The product is purified by recrystallization, vacuum dried, and ground to a fine powder. This diamidediol monomer is then polymerized with triglycolyl chloride as in Example 1.

Example 6

Poly[2,5-dioxahexane-1,6-di(carbonyloxy)decane-1,
10-di(amidocarbonylmethylene-1,4-phenylene)]

1,4-Di(4-hydroxyphenylacetamido)decane is prepared by heating 2 moles of 4-hydroxyphenylacetic acid with one mole of decanediamine with distillation of water. The product is purified by recrystallization, vacuum dried, ground to a fine powder, and polymerized with triglycolyl chloride as in Example 1.

Example 7

Poly[2,5-dioxahexane-1,6-di(carbonyloxy)hexane-1,
6-di(amidocarbonylmethyleneoxyhexamethylene)]

Hydroxyhexamethyleneoxyacetic acid is prepared in a manner similar to the preparation of hydroxyethoxyacetic acid described in Example 4 except that 1-6-hexanediol is used in place of ethylene glycol in the reaction in which sodium is reacted with the glycol followed by the addition of chloroacetic acid. Di(hydroxyhexamethyleneoxyacetamido)hexane is prepared by heating 2 moles of hydroxyhexamethyleneoxyacetic acid with one mole of hexamethylenediamine with distillation of water. The product is purified by recrystallization and vacuum dried. This diamidediol monomer is then polymerized with triglycolyl chloride as in Illustraton 1.

Example 8

Poly[2,5-dioxahexane-1,6-di(carbonyloxy)hexane-1,
6-di(amidocarbonylpentamethylene)]

1,6-Di(6-hydroxycaproamido)hexane prepared according the procedure in U.S. Pat. No. 3,025,323 is polymerized with triglycolyl chloride as in Example 1.

Example 9

Poly[2,5-dioxahexane-1,6-di(carbonyloxy)hexane-1,
6-di(amidocarbonyltetramethyleneoxyethylene)]

Hydroxyethoxyvaleric acid is prepared by in a manner similar to the preparation of hydroxyethoxyacetic acid except that 5-chlorovaleric acid is used in place of chloroacetic acid. 1,6-Di(hydroxyethoxyvaleramido)hexane is prepared by heating 2 moles of hydroxyethoxyvaleric acid with one mole of hexamethylenediamine with distillation of water. The product is purified by recrystallization and vacuum dried. This diamidediol monomer is then polymerized with triglycolyl chloride as in Example 1.

Example 10

Poly[2,5-dioxahexane-1,6-di(carbonyloxy)hexane-1,
6-di(amidocarbonyl-1,4-
phenyleneoxyhexamethylene)]

4-Hydroxy(hexamethyleneoxy)benzoic acid is prepared in a manner similar to the preparation of hydroxyhexamethyleneoxyacetic acid except that 4-chlorobenzoic acid is used in place of chloroacetic acid. This diamidediol monomer is then polymerized with triglycolyl chloride as in Example 1.

Examples 11–17

The polymers described in Examples 4–10 above, respectively, are prepared by the method described in Example 2 above to give the corresponding 1,6-hexanediol terminated polymers.

Example 18

1,6-Hexanediol terminated poly N,N'-bis
(hexamethylene)oxamido triglycolate

N,N'-bis(6-hydroxyhexamethylene)oxamide prepared according to the procedure in U.S. Pat. No. 4,226,243 Example 3 is reacted with 1,6-hexanediol and diethyl triglycolate, as a substitute for diethyl oxalate, according to the procedure in U.S. Pat. No. 4,226,243 Example 6 parts B and C.

Examples 19–26

The polymers described in Examples 11–18 above, respectively, are further reacted with glycolide as described in Example 3 above to give the corresponding polyglycolide block copolymers.

Example 27

Block copolymer of polylactide with poly[2,5-
dioxahexane-1,6-di(carbonyloxy)hexane-1,6-di
(amidocarbonylmethylene)]

Example 3 is repeated with the substitution of L-lactide for glycolide.

Example 28

Block copolymer of epsilon-caprolactone with poly
[2,5-dioxahexane-1,6-di(carbonyloxy)hexane-1,6-di
(amidocarbonylpentamethylene)]

The polymer of Example 15, i.e. 1,6-hexanediol terminated poly[2,5-dioxahexane-1,6-di(carbonyloxy)hexane-1, 6-di(amidocarbonylpentamethylene)] is further polymerized with epsilon-caprolactone according to the procedure in Example 3 with the substitution of epsilon-caprolactone for glycolide.

Example 29

Block copolymer of ρ-dioxanone and trimethylene
carbonate with poly[2,5-dioxahexane-1,6-di
(carbonyloxy)hexane-1,6-di
(amidocarbonylmethylene)]

Example 3 is repeated with the substitution of a mixture of trimethylene carbonate and ρ-dioxanone for glycolide.

Example 30

1,6-Hexanediol terminated poly[2,13-
dioxatetradecane-1,14-di(carbonyloxy)ethane-1,2-di
(amidocarbonylmethylene)]

Example 2 is repeated with the substitution of 3,14-dioxahexadecanedioic acid for 3,6-dioxaoctanedioic acid and the substitution of 1,2-di(hydroxyacetamido)ethane for 1,6-di(hydroxyacetamido)hexane.

Example 31

Growth factor-releasing bioabsorbable fiber-
reinforced implant for bone regeneration The polymer of Example 27 is extruded into multifilament yarn and hot drawn to produce high tenacity fiber via the development of molecular orientation and strain-induce crystallization. The yarn is then cut into short staple fibers of about 2 to 15 mm length and formed into an air-laid or wet-laid web by standard nonwoven fiber processing techniques. A solution of the same polymer is prepared by heating and dissolving the polymer in anhydrous N-methyl-2-pyrollidinone and cooling to room temperature. Finely divided recombinant human bone morphogenic protein is homogeneously dispersed in this solution and the mixture is then impregnated into the above fabric. The soaked fabric is then subjected to low temperature vacuum drying such that the solvent is slowly and completely evaporated. These conditions are optimized such that the solvent mixture does not dissolve or weaken the fibers in the fabric but instead causes the fibers to become bonded into a highly porous, three-dimensionally stable tissue regeneration matrix. The fabric is cut into appropriate sizes and then packaged and sterilized by ethylene oxide.

This material when implanted as a space-filling device in a bone defect induces new bone formation under the influence of the slowly released bone growth factor. The strength of the fiber-reinforced structure meanwhile maintains an appropriate matrix porosity during the bone formation process. Ultimately the implant is completely bioabsorbed and replaced with normal remodeled bone.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

What is claimed is:

1. A bioabsorbable polymer comprising a poly(ester-amide) of the general formula (I):

$$H-[E^1]_m-O-A-[O-\overset{O}{\overset{\|}{C}}-CH_2-O-(CH_2)_x-O-CH_2-\overset{O}{\overset{\|}{C}}-O-A]_p-O-[E^2]_n-H$$

wherein, x is from 2 to 10, m and n are independently from 0 to 2000, p is from 10 to 2000, and A is comprised of from 0 to 90 mole %

A1 in combination with other structures selected from the group consisting of A2 and A3, wherein:

A1 is defined by formula (II): $-(CH_2)_y-$, wherein y is from 2 to 10;

A2 is defined by formula (III):

$$-R^1-\overset{O}{\overset{\|}{C}}-NH-R^2-NH-\overset{O}{\overset{\|}{C}}-R^1-,$$

wherein:
$R^1$ is selected from the group consisting of:
 i) a linear alkene having from 1 to 5 carbon atoms;
 ii) an ester defined by formula(IV): $-(CH_2)_{x1}-O-(CH_2)_{y1}-$, wherein the $-(CH_2)_{x1}$ end of the ester is attached to the amide carbonyl of formula (III), x1 is from 1 to 4 and y1 is independently from 2 to 6;
 iii) a benzyl alkane of formula(V): $-(CH_2)_{x2}-C_6H_4-$ wherein the $-(CH_2)_{x2}$ end of the benzyl alkane is covalently attached to the amide carbonyl of formula III, and x2 is from 0 to 1; and
 iv) an alkyl benzyl ether of formula(VI): $-(CH_2)_{x3}-C_6H_4-O-(CH_2)_{y3}-$, wherein the $-(CH_2)_{x3}$ end of the alkyl benzyl ester is attached to the amide carbonyl of formula III, x3 is from 0 to 1, the $(CH_2)_{y3}-$ end of the alkyl benzyl ester is attached to the ester oxygen of formula I, and y3 is independently from 2 to 6; and $R^2$ is selected from the group consisting of linear alkylenes having from 2 to 10 carbon atoms; and A3 is defined by formula (VI):

$$-R^3-NH-\overset{O}{\overset{\|}{C}}-\overset{O}{\overset{\|}{C}}-NH-R^3-$$

wherein $R^3$ is a divalent aliphatic or aromatic hydrocarbon radical having from 3 to about 8 carbon atoms; and $E^2$ is defined by a formula selected from the group of formulae consisting of:
 formula (VII): $[-CO-CHR^4-O-]$, wherein $R^4$ is selected from the group consisting of $-H$ (from glycolide) and $-CH_3$ (from lactide);
 formula (VIII): $[-CO-O-(CH_2)_3-O-]$;
 formula (IX): $[-CO-CH_2-O-(CH_2)_2-O-]$;
 formula (X): $[-CO-(CH_2)_5-O-]$; and
 combinations of formula VII to X; and $E^1$ has the same structure as $E^2$ except that the orientation of the formula of $E^1$ is reversed.

2. The polymer of claim 1, wherein n and m have an average value between about 50 and about 1000, and p has an average value between about 20 and about 1000.

3. The polymer of claim 1 wherein A1 is formed from 1,6-hexanediol.

4. The polymer of claim 1 wherein A is formed from 1,6-di(hydroxyacetamido)hexane.

5. The polymer of claim 1 wherein A is formed from N,N'-bis(6-hydroxyhexamethylene)oxamide.

6. The polymer of claim 1 wherein A is formed from 1,6-di(6-hydroxycaproamido)hexane.

7. The polymer of claim 1 characterized in that the poly(ester-amide) of formula (I) is prepared by:
a) reacting a linear aliphatic diamine of 2 to 10 methylene carbon atoms with a lactone or a hydroxyacid selected from the following formulae:

formula (a-I):

$$O=C-O-(CH_2)_x$$

wherein x is from 2 to 5;
formula (a-II): $HO-R^1-COOH$
wherein $R^1$ is selected from the group consisting of:
 i) linear alkylenes having from 1 to 5 carbon atoms; and
 ii) $-(CH_2)_x-O-(CH_2)_y-$ wherein x (the end attached to the carbonyl) is from 1 to 4 and y (the end attached to the oxygen) is independently from 2 to 6;
 iii) $-(CH_2)_x-C_6H_4-$ wherein x (the end attached to the carbonyl) is from 0 to 1; and
 iv) $-(CH_2)_x-C_6H_4-O-(CH_2)_y-$ wherein x (the end attached to the carbonyl) is from 0 to 1 and y (the end attached to the oxygen) is independently from 2 to 6 to produce a diamidediol; and b) melt polyesterifying the diamediol by reacting said diamidediol with 3,6-dioxaoctanedioic acid, its diacid chloride, dimethyl ester, or diethyl ester derivatives to produce the poly(ester-amide).

8. The polymer of claim 1 characterized in that the poly(ester-amide) of formula (I) is prepared by:

a) providing a diamidediol of the following structure:
HO—R—NH—CO—CO—NH—R—OH, wherein R is a divalent aliphatic or aromatic hydrocarbon radical having from 3 to about 8 carbon atoms; and b) melt polyesterifying the diamediol by reacting said diamidediol with 3,6-dioxaoctanedioic acid, its diacid chloride, dimethyl ester, or diethyl ester derivatives to produce the poly(ester-amide).

9. A bioabsorbable surgical suture made from a polymer of claim 1.

10. A bioabsorbable polymer comprising a poly(ester-amide) of the general formula (XV):

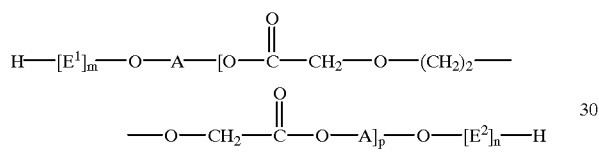

wherein, m and n are independently from 0 to 2000, p is from 10 to 2000, and A is comprised of from 0 to 90 mole %

A1 in combination with other structures selected from the group consisting of A2 and A3, wherein:
A1 is defined by formula (II): —(CH$_2$)$_y$—, wherein y is from 2 to 10;
A2 is defined by formula (III):

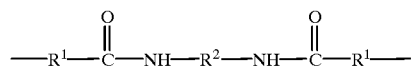

wherein: R$^1$ is selected from the group consisting of:
i) a linear alkene having from 1 to 5 carbon atoms;
ii) an ester defined by formula(IV): —(CH$_2$)$_{x1}$—O—(CH$_2$)$_{y1}$—, wherein the —(CH$_2$)$_{x1}$ end of the ester is attached to the amide carbonyl of formula (III), x1 is from 1 to 4 and y1 is independently from 2 to 6;
iii) a benzyl alkane of formula(V):

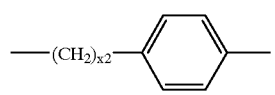

wherein the —(CH$_2$)$_{x2}$ end of the benzyl alkane is covalently attached to the amide carbonyl of formula III, and x2 is from 0 to 1; and iv) an alkyl benzyl ether of formula(VI):

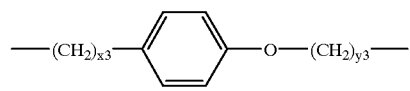

wherein the —(CH$_2$)$_{x3}$ end of the alkyl benzyl ester is attached to the amide carbonyl of formula III, x3 is from 0 to 1, the (CH$_2$)$_{y3}$— end of the alkyl benzyl ester is attached to the ester oxygen of formula I, and y3 is independently from 2 to 6; and
R$^2$ is selected from the group consisting of linear alkylenes having from 2 to 10 carbon atoms; and
A3 is defined by formula (VI):

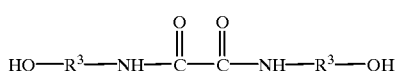

wherein R$^3$ is a divalent aliphatic or aromatic hydrocarbon radical having from 3 to about 8 carbon atoms; and E$^2$ is defined by a formula selected from the group of formulae consisting of:
formula (VII): [—CO—CHR$^4$—O—], wherein R$^4$ is selected from the group consisting of —H (from glycolide) and —CH$_3$ (from lactide);
formula (VIII): [—CO—O—(CH$_2$)$_3$—O—];
formula (IX): [—CO—CH$_2$—O—(CH$_2$)$_2$—O—];
formula (X): [—CO—(CH$_2$)$_5$—O—]; and
combinations of formula VII to X; and E$^1$ has the same structure as E$^2$ except that the orientation of the formula of E$^1$ is reversed.

11. The polymer of claim 10 characterized in that the poly(ester-amide) of formula (XV) is prepared by:

a) reacting a linear aliphatic diamine of 2 to 10 methylene carbon atoms with a lactone or a hydroxyacid selected from the following formulae:

formula (a-I):

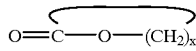

wherein x is from 2 to 5;
formula (a-II): HO—R$^1$—COOH
wherein R$^1$ is selected from the group consisting of:
i) linear alkylenes having from 1 to 5 carbon atoms;
ii) —(CH$_2$)$_{x1}$—O—(CH$_2$)$_{y1}$—, wherein the —(CH$_2$)$_{x1}$ end is attached to the carbonyl of formula (a-II), x1 is from 1 to 4 and y1 is independently from 2 to 6;

iii)

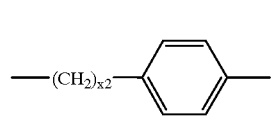

wherein the —(CH$_2$)$_{x2}$ end is attached to the carbonyl of formula (a-II), x2 is from 0 to 1; and

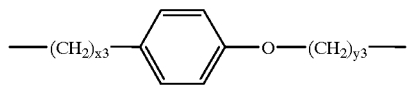

wherein the —$(CH_2)_{x3}$ end is attached to the carbonyl of formula (a-II), x3 is from 0 to 1, and y is independently from 2 to 6; to produce a diamidediol; and b) melt polyesterifying the diamediol by reacting the diamidediol with a reagent selected from the group consisting of: 3,6-dioxaoctanedioic acid, its diacid chloride, dimethyl ester, and diethyl ester derivatives to produce a poly(ester-amide) polymer of formula(I).

12. The polymer of claim 7, wherein the polymer is a block copolymer prepared by further reacting said poly (ester-amide) with glycolide, lactide, trimethylene carbonate, ρ-dioxanone, or epsilon-caprolactone or combinations thereof to produce a block copolymer.

13. The polymer of claim 11, wherein the polymer is a block copolymer prepared by further reacting said poly (ester-amide) with glycolide, lactide, trimethylene carbonate, ρ-dioxanone, or epsilon-caprolactone or combinations thereof.

* * * * *